United States Patent [19]

Schnur

[11] Patent Number: 4,617,312

[45] Date of Patent: Oct. 14, 1986

[54] ALDOSE REDUCTASE INHIBITING 5-(2-ALKOXYPHENYL) THIAZOLIDINEDIONES

[75] Inventor: Rodney C. Schnur, Noank, Conn.

[73] Assignee: Pfizer Inc., New York, N.Y.

[21] Appl. No.: 692,252

[22] Filed: Jan. 17, 1985

Related U.S. Application Data

[63] Continuation-in-part of Ser. No. 458,684, Jan. 17, 1983, abandoned.

[51] Int. Cl.[4] .................. C07D 277/34; A61K 31/425
[52] U.S. Cl. ...................................... 514/369; 548/183
[58] Field of Search ........................ 548/183; 514/369

[56] References Cited

FOREIGN PATENT DOCUMENTS 889757 1/1982 Belgium .
33617 8/1981 European Pat. Off. .
57-028073 2/1981 Japan .

OTHER PUBLICATIONS

Sohda et al., Chem. Pharm. Bull. 30, 3601–3616 (1982).

*Primary Examiner*—Robert Gerstl
*Attorney, Agent, or Firm*—Charles J. Knuth; Peter C. Richardson; Robert F. Sheyka

[57] ABSTRACT

A series of 5-(2-alkoxyphenyl)thiazolidinediones and pharmaceutically acceptable salts thereof useful as hypoglycemic agents, aldose reductase inhibitors and as therapeutic agents for the treatment of chronic diabetic complications; intermediates therefore; and process for preparation of said compounds.

12 Claims, No Drawings

ALDOSE REDUCTASE INHIBITING 5-(2-ALKOXYPHENYL) THIAZOLIDINEDIONES

CROSS-REFERENCE TO RELATED APPLICATIONS

This application is a continuation in part of copending application Ser. No. 458,684 filed Jan. 17, 1983 now abandoned.

BACKGROUND OF THE INVENTION

This invention relates to novel 5-(2-alkoxyphenyl)-thiazolidinediones and to pharmaceutically acceptable salts thereof useful as hypoglycemic agents, inhibitors of aldose reductase and as therapeutic agents for the treatment of chronic diabetic complications.

Despite the widespread use of insulin and of the availability of a large number of synthetic hypoglycemic agents such as the sulfonylureas (e.g chlorpropamide, tolbutamide, acetohexamide) and biganides (e.g. phenformin), the search for improved hypoglycemic agents continues. More recently, efforts have been directed to controlling certain chronic complications of diabetes, such as diabetic cataracts, neuropathy and retinopathy. Such efforts have given rise to development of aldose reductase inhibitors, compounds which inhibit the activity of the enzyme aldose reductase which is primarily responsible for regulating reduction of aldoses to the corresponding polyols. In this way, unwanted accumulation of galactitol in the lens of galactosemic subjects and of sorbitol in the lens, kidney and peripheral nervous cord of various diabetic subjects is prevented or reduced. References which describe aldose reductase inhibitors are U.S. Pat. No. 3,821,383, 1,3-dioxo-1H-benz[d,e]-isoquinoline-2(3H)-acetic acid and related compounds; U.S. Pat. No. 4,200,642 - spiro-oxazolidine-24-diones; U.S. Pat. Nos. 4,117,230; 4,130,714; 4,147,797; 4,210,756; 4,235,911 and 4,282,229 each of which describes certain spirohydantoins. Belgian Pat. Nos. 889,757 and 889,758 describe 5-(substituted phenyl)oxazolidine-2,4-diones as hypoglycemic agents.

European Patent Application 33,617 published Aug. 12, 1981 describes certain 5-(disubstituted phenyl)-thiazolidine-2,4-diones which exhibit activity to control chronic diabetic complications. A variety of 5-(4-alkoxybenzyl)thiazolidine-2,4-diones having hypolipidemic and hypoglycemic activities are disclosed in European Patent Application No. 8203 published Feb. 20, 1980.

Sohda et al., Chem. Pharm. Bull. 30,3601-16 (1982) report on the hypoglycemic and hypolipedemic properties of thiazolidine-2,4-diones having at the 5-position one or two substituents such as phenyl, heteryl or alkyl. Many of the same compounds are disclosed in Japanese Patent Application No. 57,028,073, published Feb. 15, 1982.

SUMMARY OF THE INVENTION

It has now been found that certain 5-(2-alkoxyphenyl)thiazolidinediones of formula I below and pharmaceutically acceptable salts thereof are useful as hypoglycemic agents, aldose reductase inhibitors and as therapeutic agents for the prevention and/or alleviation of chronic diabetic complications.

The present invention is concerned with compounds of the formula

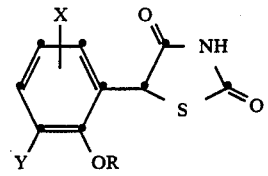

and the base salts thereof with pharmacologically acceptable cations, wherein

R is alkyl having from one to four carbon atoms;
X is fluoro, chloro or bromo at any one of positions 4, 5 or 6 in the phenyl ring; and
Y is hydrogen, chloro, lower alkyl or lower alkoxy, provided that when Y is hydrogen then X is not 4-chloro.

The preferred compounds are those wherein X is fluoro or chloro, Y is methyl, and R is methyl; and those wherein X is 5- or 6-chloro, Y is hydrogen, and R is methyl.

Because of the acidic hydrogen atom in the thiazolidinedione ring of the compounds of formula I, salts can be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkanol solution of the compound of formula I may be mixed with an alkoxide of the desired metal and the solution subsequently evaporated to dryness. Suitable pharmaceutically acceptable cations for this purpose include, but are not limited to, potassium, sodium, ammonium, calcium and magnesium, aluminum, benzathine, piperazine, N-methylglucamine and procaine.

Also embraced by the present invention are pharmaceutical compositions comprising a pharmaceutically acceptable carrier and a compound of formula I in an amount effective for the treatment of hyperglycemia and diabetes-associated complications, including diabetic cataracts, neuropathy and retinopathy. Preferred compounds for use in such pharmaceutical compositions are those having the preferred substituents as defined above.

The present invention further includes a method of treatment of hyperglycemia and diabetes-associated complications, including diabetic cataracts, neuropathy and retinopathy, which comprises administering to a subject in need of treatment an effective amount of a compound of formula I, preferably a compound having the preferred substituents as defined above.

DETAILED DESCRIPTION OF THE INVENTION

The novel compounds (IV) of this invention are prepared according to the reaction sequence presented below.

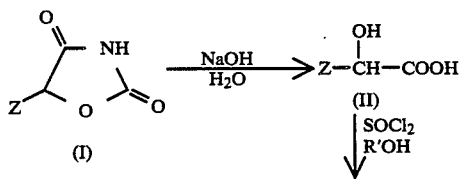

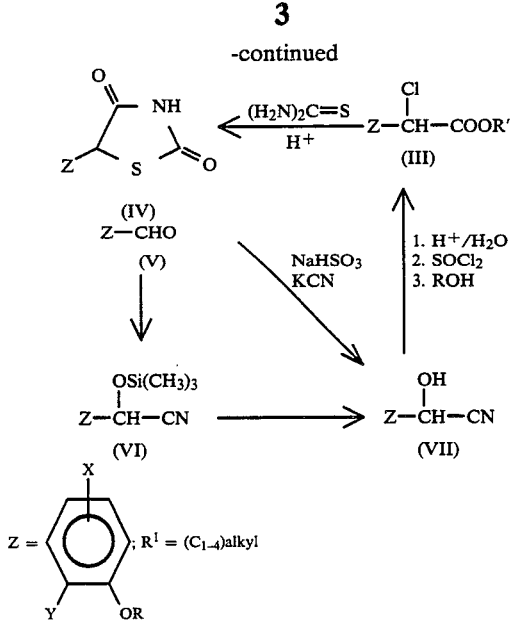

A favored procedure comprises reaction of the appropriate alpha-(2-alkoxyphenyl)-alpha-chloroacetic acid alkyl ester (III) with thiourea in a reaction-inert solvent, e.g. ethanol, isopropanol, sulfolane, at a temperature of 75° C. or higher. The 5-(2-alkoxyphenyl)-2-iminothiazolidin-4-one thus produced is then hydrolyzed with dilute aqueous acid, such as 2-6N HCl, in a solvent such as ethanol, to produce (IV) which is isolated by known procedures.

The alpha-(2-alkoxyphenyl)-alpha-chloroacetic acid alkyl esters (III) required as starting materials are prepared by hydrolysis of the appropriate 5-(2-alkoxyphenyl)oxazolidine-2,4-dione (I) under alkaline conditions in a suitable solvent such as ethanol at or near the reflux temperature. The hydrolysis reaction is usually complete in 2 to 4 hours. The alpha-(2-alkoxyphenyl)-alpha-hydroxy acetic acid (II) is recovered by acidification of the reaction mixture and extraction of the desired product with, for example, ethyl acetate.

The thus-obtained acid (II) is then reacted with thionyl chloride or POCl₃ to produce the corresponding alpha-chloroacetic acid chloride derivative which is then esterified by reaction with the appropriate ($C_{1-4}$)alcohol to afford (III).

Many of the 5-(2-alkoxyphenyl)oxazolidine-2,4-dione reactants are described in Belgian Pat. No. 889,757.

Alternatively, the alpha-(2-alkoxyphenyl)-alpha-chloroacetic acid alkyl esters are prepared from the appropriate benzaldehyde (V). The procedure comprises conversion of the benzaldehyde to the cyanohydrin (VII) via the bisulfite adduct which is reacted with cyanide in a two phase, aqueous-organic solvent system. In a modification of this procedure, the aldehyde is first converted to the trimethylsilyl cyanohydrin (VI) by reaction with trimethylsilylcarbonitrile, in the presence of a catalytic amount of a Lewis acid, e.g., zinc iodide. A reaction inert solvent (e.g. methylene chloride, ether) is generally used when the aldehyde is a solid, but is optional when the aldehyde is a liquid. The temperature of the reaction is not critical, it being conveniently made up at reduced temperature (e.g. 0°-25° C.) and allowed to proceed at room temperature for a matter of hours or days, as necessary to achieve complete reaction. The trimethylsilyl ether is then hydrolyzed to cyanohydrin (VI), conveniently at reduced temperature (e.g. 0° C.) in a two phase strong aqueous acid/organic solvent system.

The cyanohydrin (VII) is conveniently hydrolyzed to the corresponding hydroxy acid by reaction with excess concentrated hydrochloric acid in formic acid, generally at the reflux temperature of the solvent system. Likewise the trimethylsilyl cyanohydrin may be hydrolyzed directly to the hydroxy acid by the above formic acid procedure. The hydroxy acid is isolated by known methods. It is converted to the alpha-chloro acetic acid alkyl ester (III) according to the procedure described above for converting (II) to (III).

The aldehydes (V) required for the above syntheses are broadly available either commercially, or by literature methods, such as those described in Belgian Pat. No. 889,757.

The compounds of formula I and the pharmaceutically acceptable salts thereof are useful as inhibitors of the enzyme aldose reductase in the treatment (i.e. prevention and alleviation) of chronic complications of diabetes, such as diabetic cataracts, retinopathy and neuropathy. They are administered alone or in combination with pharmaceutically acceptable carriers in single or multiple doses to a subject in need of treatment by a variety of conventional routes of administration, including oral, parenteral and topical, including ophthalmic. In general, these compounds will be administered orally or parenterally at dosages between about 0.25 and 25 mg/kg body weight of the subject to be treated per day, preferably from about 1.0 to 10 mg/kg.

Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients, disintegrants, binding agents and lubricating agents can be used. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, together with diluents such as water, ethanol, propylene glycol, glyercine and combinations thereof.

For parenteral administration, solutions of the novel compound of formula I in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Preparations suitable for ophthalmic use, especially for treatment of diabetic cataracts, will contain a compound of formula I or a pharmaceutically acceptable salt thereof in a concentration from about 0.1 to about 5% by weight, preferably from about 0.5 to about 2% in a pharmaceutically acceptable solution, suspension or ointment. Ophthalmic preparations, prepared in accordance with conventional pharmaceutical practice, will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Regardless of the route of administration used, some variation in the concentration ranges specified herein will necessarily occur, depending on the particular compound used and the condition of the person to be treated. In any event, the person responsible for administration will determine the appropriate dose for the individual subject.

The activity of the compounds of the present invention as agents for the control of chronic diabetic complications can be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats. Suitable experimental procedures are described in U.S. Pat. No. 3,821,383 and the references cited therein.

The compounds of the present invention are readily adapted to clinical use as antidiabetic agents. The hypoglycemic activity required for this clinical use is defined by the glucose tolerance test procedure which follows. Intact male albino rats are fasted approximately 18–24 hours, then weighed, numbered and recorded in groups of five or six as needed. Each group of animals is then dosed intraperitoneally with glucose (one gram per kilogram) and orally with either water (controls) or compound (at a level usually selected from the range 0.1 to 100 mg/kg). Blood glucose levels (mg/100 ml) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test. A blood glucose lowering of 9% or greater generally reflects statistically significant hypoglycemic activity in this test.

They are clinically administered to mammals, including man, via either the oral or the parenteral route. Administration by the oral route is preferred, being convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.25 to about 25 mg/kg body weight of the subject per day, preferably about 1.0 to about 10 mg/kg body weight per day administered singly or as a divided dose.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

In the examples which follow, no effort was made to optimize the yields of a given reaction.

EXAMPLE 1

5-(6-Chloro-2-Methoxyphenyl)-Thiazolidine-2,4-Dione

A mixture of methyl alpha-chloro-alpha-(6-chloro-2-methoxyphenyl)acetate (1.37 g, 5.5 mmoles), thiourea (0.84 g, 10.0 mmoles) and ethanol (10 ml) was refluxed for 16 hours. Concentrated hydrochloric acid (4 ml) was added to the mixture and refluxing continued for an additional 16 hours. An additional 2 ml of concentrated hydrochloric acid was added and the mixture refluxed for 16 more hours. The yellow solution was then cooled to room temperature and poured into 150 ml of water. The title product was isolated by extraction of the aqueous mixture with ethyl acetate (2×150 ml). The extract was washed with water (1×50 ml) and brine (1×50 ml), then dried (MgSO$_4$) and concentrated in vacuo to a brown oil (0.91 g). Trituration of the oil in hexane (50 ml) gave a solid which was recrystallized from ethanol-water (1:1) as a white solid, 0.0719 g. M.P. 195°–197° C.

The compounds tabulated were prepared in like manner from the appropriate methyl alpha-chloro-alpha-(2-alkoxyphenyl)acetate reactant.

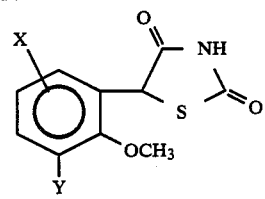

| Reactant Z—CH(Cl)COOCH$_3$ | | | Product | | | |
|---|---|---|---|---|---|---|
| Ex. | Z | GMS | X | Y | GMS | MP (°C.) |
| 2 | 6-F—2-OCH$_3$—C$_6$H$_3$ | 1.19 | 6-F | H | 0.0723 | 127.0–128.5 |
| 3 | 5-Cl—2-OCH$_3$—C$_6$H$_3$ | 1.00 | 5-Cl | H | 0.3018 | 237–238 |

-continued

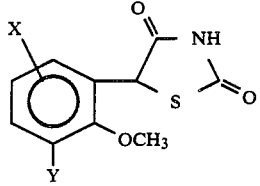

| | Reactant Z—CH(Cl)COOCH₃ | | Product | | | |
|---|---|---|---|---|---|---|
| Ex. | Z | GMS | X | Y | GMS | MP (°C.) |
| 4 | 5-Cl—2-OCH₃—3-CH₃—C₆H₂ | 0.92 | 5-Cl | CH₃ | 0.032 | 160–163 |

EXAMPLE 5

Following the procedure of Example 1, the compounds tabulated below are prepared from the appropriate reactants of Preparation F.

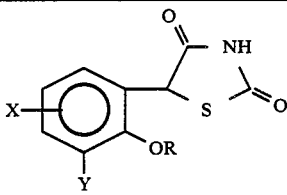

| R | Y | X |
|---|---|---|
| C₂H₅ | H | 6-F |
| CH₃ | H | 5-Br |
| C₂H₅ | H | 5-Cl |
| C₂H₅ | H | 5-F |
| CH₃ | Cl | 5-F |
| C₂H₅ | H | 5-Br |
| CH₃ | OCH₃ | 5-Br |
| CH₃ | H | 4-Cl |
| CH₃ | H | 5-Cl |

EXAMPLE 6

The sodium salts of the products of Examples 1–5 are prepared by dissolving said compound in water containing an equivalent amount in moles of sodium hydroxide and then freeze-drying the mixture. In this way, the desired alkali metal salt of the thiazolidinedione is obtained in the form of an amorphous powder which is freely soluble in water.

In like manner, the potassium and lithium salts are also similarly prepared.

PREPARATION A

Methyl alpha-Chloro-alpha-(6-Chloro-2-Methoxyphenyl)Acetate

A mixture of 5-(6-chloro-2-methoxyphenyl)oxazolidine-2,4-dione (2.20 g, 9.10 mmoles), aqueous sodium hydroxide (5.4 ml of 6N, 32.3 mmoles) and ethanol (6 ml) was heated in a 90° C. oil bath for 24 hours, then stirred at room temperature for 48 hours. The black reaction mixture was then poured into 150 ml of water and the pH of the aqueous mixture adjusted to pH 2 by addition of 1N HCl. Extraction of the acidified aqueous solution with diethyl ether (2×150 ml), followed by washing the combined extract with brine (2×200 ml), drying (MgSO₄) and concentration of the dried extract gave a brown oil. Trituration of the oil with hexane (2×100 ml) gave 0.69 g of a tan solid; m.p. 139.5°–142° C., the acid form of the title compound. Additional acid was isolated by extraction of the acidified aqueous solution with ethyl acetate (2×200 ml). The pooled ethyl acetate extracts were washed with brine (1×100 ml), dried (MgSO₄) and concentrated to an oil. Trituration of the oil with hexane (2×100 ml) gave a white solid (0.75 g).

The combined acid product (1.40 g, 6.46 mmoles) was reacted with thionyl chloride (5.0 ml) at 30° C. for five hours after which the excess thionyl chloride was stripped under reduced pressure. Methanol (5.0 ml) was added and the red solution stirred at ambient temperature for ten minutes. Water (50 ml) was then added and the resulting solution extracted with ethyl acetate (2×100 ml). The extracts were combined, washed successively with 5% sodium bicarbonate solution (2×50 ml), water (1×50 ml) and brine (1×50 ml), and then dried (MgSO₄). Concentration of the dried extract gave the title product as a brown oil (1.37 g). It was used as is.

By means of the above procedures, the compounds tabulated below were prepared as brown oils from the appropriate 5-(2-alkoxyphenyl)oxazolidine-2,4-dione. They were used directly without purification to prepare the 5-(2-alkoxyphenyl)thiazolidine-2,4-diones of Examples 2 and 3:

methyl alpha-chloro-alpha-(6-fluoro-2-methoxyphenyl)acetate methyl alpha-chloro-alpha-(5-chloro 2-methoxyphenyl)acetate.

PREPARATION B

The following compounds are prepared from the corresponding 5-(2-alkoxyphenyl)oxazolidine-2,4-diones according to the procedure of Preparation A.

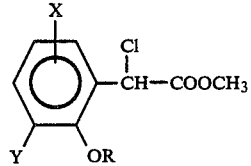

| R | Y | X |
|---|---|---|
| C₂H₅ | H | 6-F |
| CH₃ | H | 5-Br |
| C₂H₅ | H | 5-Cl |
| C₂H₅ | H | 5-F |
| CH₃ | Cl | 5-F |

PREPARATION C

2-Methyl-4-Chloroanisole

To a suspension of 2-methoxy-5-chlorobenzaldehyde (34.5 g, 0.202 mole) in bis-(2-hydroxyethyl)ether (225 ml) was added hydrazine hydrate (17.7 g, 0.353 mole) and the mixture heated on a 125° C. oil bath for 15 minutes. It was then cooled to 50° C. and powdered potassium hydroxide (15.5 g of 85%, 0.24 mole) added. The mixture was heated on a 165° C. oil bath for 30 minutes. After it had cooled to room temperature it was poured into water (600 ml) and the aqueous solution acidified by addition of 6N HCl. Carbon tetrachloride (4×100 ml) extractions of the acid solution, followed by washing the pooled extracts with brine (1×100 ml), drying (MgSO$_4$) and concentration in vacuo gave a clear viscous oil which crystallized upon addition of a small volume of petroleum ether and chilling in an ice bath. The white crystals were filtered and dried in vacuo. Yield=24.7 g (78%); m.p. 35°-37° C.

PREPARATION D

5-Chloro-2-Methoxy-3-Methylbenzaldehyde

Titanium tetrachloride (21.6 g, 0.114 mole) was added to a solution of 2-methyl-4-chloroanisole (9 g, 0.057 mole) in methylene chloride at 0° C. Then, 1,1-dichloromethyl methyl ether (7.24 g, 0.063 mole) was added dropwise over a three minute period and the reaction mixture stirred at 0° C. for 30 minutes. The reaction was quenched by carefully pouring it into water (600 ml). The organic layer was separated and the aqueous phase extracted with methylene chloride (2×100 ml). The combined organic layer and extracts was washed with brine, dried (MgSO$_4$) and concentrated under reduced pressure to a pale yellow solid (10.1 g).

The crude product was purified by column chromatography in an 80 mm diameter flash column packed with 10″ of 230-400 mesh silica gel. Elution of the column with 90 hexane/10 ether gave the title product (3.65 g); m.p. 92°-94° C.

PREPARATION E alpha-Hydroxy-(2-Methoxy-3-Methyl-5-Chlorobenzyl)cyanide

To a solution of sodium bisulfite (676 mg, 6.50 mmoles) in water (6 ml) at 60° C. was added 5-chloro-2-methoxy-3-methylbenzaldehyde (10 g, 5.42 mmoles). The mixture was stirred for one hour, cooled to 0° C., and ether (6 ml) added. Sodium cyanide (292 mg, 5.96 mmoles) in water (6 ml) was added to the reaction mixture dropwise with stirring. The reaction was stirred for two hours during which time it was allowed to reach room temperature. The ether layer was separated, and the aqueous phase extracted with ether (2×50 ml). The combined ether extracts were dried (MgSO$_4$) and concentrated to give 970 mg (84%) of the cyanohydrin product which was used directly for preparing the corresponding acid.

PREPARATION F alpha-Hydroxy-alpha-(5-Chloro-2-Methoxy-3-Methylphenyl)Acetic Acid

The cyanohydrin, Preparation E, (970 mg, 4.58 mmoles) in a solution of formic acid (3.5 ml) and concentrated hydrochloric acid (2.5 ml) was refluxed overnight. It was then poured into water (50 ml), the pH adjusted to 14 by addition of 6N NaOH solution and then extracted with ethyl acetate (2×100 ml). The basic aqueous solution was acidified to pH 1 by addition of 6N HCl then extracted with ethyl acetate (2×100 ml). The pooled extracts were dried (MgSO$_4$) and concentrated to give a tan solid which was washed with hexane and dried; 800 mg (73%).

It was converted to methyl alpha-chloro-alpha-(5-chloro-2-methoxy-3-methylphenyl)acetate by the chlorination/esterification procedure of Preparation A. The product was used directly to prepare the thiazolidine-2,4-dione of Example 4.

PREPARATION G

Utilizing the procedures of Preparation C-F, the following compounds are obtained from the appropriate benzaldehyde reactant.

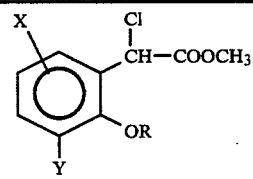

| R | Y | X |
|---|---|---|
| CH$_3$ | CH$_3$ | 5-Br |
| C$_2$H$_5$ | CH$_3$ | 5-Br |

PREPARATION H

The procedures of Preparation E and F are employed to prepare the following compounds from appropriate benzaldehyde reactants.

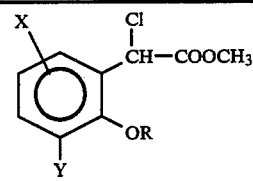

| R | Y | X |
|---|---|---|
| C$_2$H$_5$ | H | 5-Br |
| CH$_3$ | OCH$_3$ | 5-Br |
| CH$_3$ | H | 4-Cl |
| CH$_3$ | H | 5-Cl |

I claim:

1. A compound selected from the group consisting of aryl thiazolidinedione derivatives of the formula:

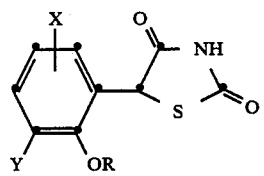

and the base salts thereof with pharmaceutically acceptable cations, wherein

R is alkyl having from one to four carbon atoms;

X is fluoro, chloro or bromo; and

Y is hydrogen, chloro, lower alkyl or lower alkoxy, provided that when Y is hydrogen then X is not 4-chloro.

2. A compound as claimed in claim 1 wherein R is alkyl having from one to four carbon atoms, X is fluoro and Y is hydrogen.

3. A compound as claimed in claim 1 wherein R is alkyl having from one to four carbon atoms, X is 5-chloro or 6-chloro and Y is hydrogen.

4. A compound as claimed in claim 1 wherein R is alkyl having from one to four carbon atoms, X is chloro and Y is lower alkyl.

5. A compound as claimed in claim 1 wherein R is alkyl having from one to four carbon atoms, X is fluoro and Y is lower alkyl.

6. 5-(6-Fluoro-2-methoxyphenyl)thiazolidine-2,4-dione.

7. 5-(6-Chloro-2-methoxyphenyl)thiazolidine-2,4-dione.

8. 5-(5-Chloro-2-methoxyphenyl)thiazolidine-2,4-dione.

9. 5-(5-Chloro-2-methoxy-3-methylphenyl)thiazolidine-2,4-dione.

10. A method for treating a diabetic host for chronic diabetes associated complications consisting of diabetic cataracts, neuropathy and retinopathy which comprises administering to said host an anti-diabetically effective amount of a compound of claim 1.

11. A pharmaceutical composition for the treatment of chronic diabetes associated complications consisting of diabetic cataracts, neuropathy and retinopathy comprising a pharmaceutically acceptable carrier and an anti-diabetically effective amount of a compound of claim 1.

12. A method of inhibiting the enzyme aldose reductase in a diabetic host requiring said treatment comprising administering to said host a compound of claim 1 in an amount effective to inhibit aldose reductase.

* * * * *